United States Patent [19]

Joslyn

[11] Patent Number: 4,770,851
[45] Date of Patent: Sep. 13, 1988

[54] METHODS FOR STERILIZATION OF MATERIALS BY CHEMICAL STERILANTS

[75] Inventor: Larry Joslyn, Macedon, N.Y.

[73] Assignee: Joslyn Valve Corp., Macedon, N.Y.

[21] Appl. No.: 883,299

[22] Filed: Jul. 7, 1986

Related U.S. Application Data

[63] Continuation of Ser. No. 678,537, Dec. 5, 1984, abandoned.

[51] Int. Cl.$^4$ .................... A61L 2/06; A61L 2/20
[52] U.S. Cl. ........................ 422/26; 422/27; 422/28; 422/34; 422/36
[58] Field of Search ................ 422/26–28, 422/31, 34, 36

[56] References Cited

U.S. PATENT DOCUMENTS

| 2,080,179 | 5/1937 | Merriam et al. | 422/27 |
| 2,241,010 | 12/1980 | Baran | 422/27 X |
| 2,868,616 | 1/1959 | Poitras | 422/26 X |
| 3,068,064 | 12/1962 | McDonald | 422/34 X |
| 3,598,516 | 8/1971 | Shull et al. | 422/27 |
| 3,954,406 | 5/1976 | Chamberlain | 422/27 |
| 4,127,384 | 11/1978 | Fahlvik et al. | 422/295 X |
| 4,203,943 | 5/1980 | Gillis et al. | 422/27 |
| 4,203,947 | 5/1980 | Young et al. | 422/26 X |
| 4,239,730 | 12/1980 | Fahlvik et al. | 422/295 X |
| 4,309,381 | 1/1982 | Champerlain et al. | 422/26 X |
| 4,447,394 | 5/1984 | Krovthén | 422/36 X |

FOREIGN PATENT DOCUMENTS

| 2844871 | 4/1979 | Fed. Rep. of Germany | 422/27 |
| 0639554 | 12/1978 | U.S.S.R. | 422/26 |
| 0001245 | 1/1888 | United Kingdom | 422/26 |
| 488638 | 7/1938 | United Kingdom . | |
| 0511179 | 8/1939 | United Kingdom | 422/26 |
| 1077246 | 7/1967 | United Kingdom | 422/34 |

OTHER PUBLICATIONS

"Practical System for Steam-Formaldehyde Sterilizing", J. K. Pickerill, Laboratory Practice, vol. 24, No. 6, Jun. 1975, pp. 401–404.

Primary Examiner—Barry S. Richman
Assistant Examiner—Jill Johnston
Attorney, Agent, or Firm—Martin LuKacher

[57] ABSTRACT

Methods for sterilization wherein air is purged from the load to be sterilized prior to the addition of the sterilant and wherein residue chemical sterilants, such as ethylene oxide, are purged post-sterilization by introducing air and steam at pressures which cause the steam to condense on the interstices of the load and then vaporize to provide a carrier for trapped air (prior to sterilization) and residue chemical sterilant (post-sterilization).

15 Claims, 2 Drawing Sheets

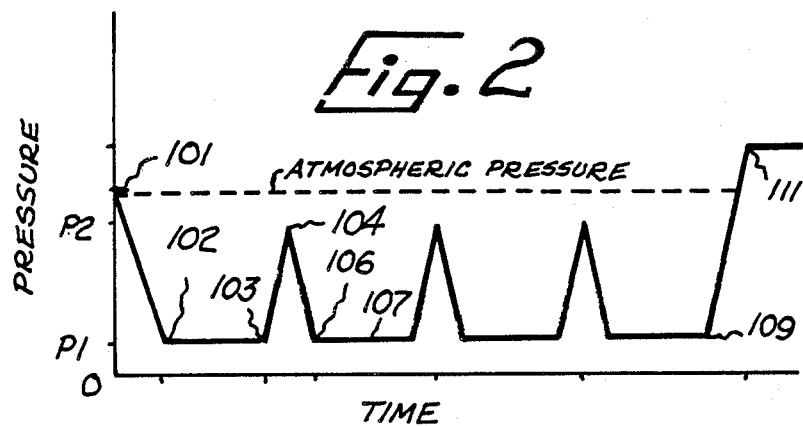
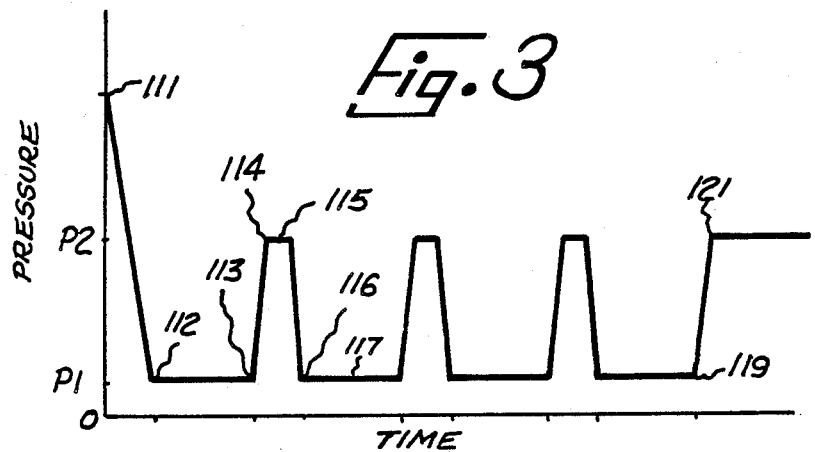
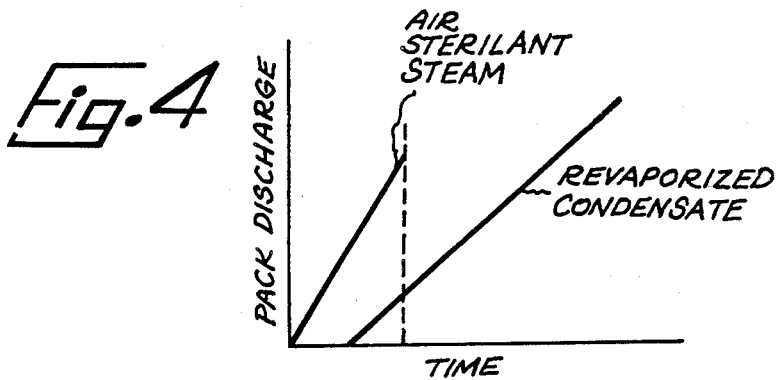

METHODS FOR STERILIZATION OF MATERIALS BY CHEMICAL STERILANTS

This is a continuation of application Ser. No. 678,537, filed Dec. 5, 1984, now abandoned.

DESCRIPTION

This invention relates to methods for the introduction and removal of chemical sterilants into and out of various materials.

The invention is especially suitable for sterilization of loads, such as towels, sheets and tubing used by hospitals, that contain voids or spaces. A major concern in sterilization with chemical sterilants is the inability of humidity and sterilant to reach and then be removed from the interstices of materials being processed.

It has been discovered, in accordance with the invention, that one key to an effective sterilization process is to remove non-condensible gas, such as air, from the materials and substitute a condensing gas, such as steam, to provide humidity and allow more effective sterilant penetration. During air removal, the pressure of the condensing gas is raised. This drives the gas into the interstices of the load. The gas, which dew points on the load, can be revaporized and will carry any non-condensing gas trapped in the interstices of the load out with it. Thus, when the chemical sterilant is admitted to the sterilizing chamber, the condensible gas again dew points on the surface of the material and allows the chemical sterilant to penetrate into the voided interstices of the materials being processed.

Another key to promote effective sterilization, which has been discovered in accordance with the invention, is to remove residue sterilant from the insterstices of the sterilized load. This can be accomplished by introducing a condensing gas, such as steam, into the interstices of the load. Pressurization of the condensing gas causes the steam to dew point on the load. The steam then can be revaporized and will carry the residue chemical sterilant in the interstices of the load out with it. The sterilized materials, therefore, are ready for immediate use.

In current chemical sterilization processes, non-condensible gases, such as air, are removed prior to introduction of a chemical sterilant by evacuating the sterilizing chamber and admitting steam at subatmospheric pressure, and then purging the chamber with steam at subatmospheric pressure. In some processes, small pressure pulses in the order of 1 psi are incorporated in the steam flush to enhance the removal of air from the interstices of the load. Because of the small pressure pulse which can be applied with steam before the chamber environment would exceed the allowable temperature for materials being processed, the removal of air from the inside of materials is very inefficient.

A second major concern is that chemical sterilants, such as ethylene oxide or formaldehyde, remain both in the sterilizing chamber and the product following sterilization. When a sterilizer is opened following sterilization, residue sterilant in the sterilizing chamber enters the working environment posing a potential health hazard to the sterilizer operator. Residue sterilant remaining in the product also poses a potential health hazard if there is physical contact with the material.

Several equipment design methods have been employed to minimize chemical sterilant residues. Post cycle pressure pulsing with air to dilute the sterilizing chamber sterilant concentration or flushing the sterilizing chamber with air are typical of these methods. This procedure does not readily remove the sterilant inside packaging materials or sterilant absorbed by the materials. Aeration (ventilated air washing) periods are required before handling or using the materials. Aeration of such materials must be performed in well vented areas to prevent the build up of sterilant in the working environment. This results in material handling logistics involving quarantine facilities as well as the necessity of environmental monitoring and control.

It is the object of the present invention to provide improved sterilization methods and apparatus for removal of air prior to sterilization, efficient humidification of the load during sterilization, and removal of the chemical sterilant from both the materials being sterilized and the sterlizing chamber in a chemical sterilization process.

It is a feature of the invention to provide a plurality of pressure pulses and steam flush periods to (a) remove non-condensible gases, such as air or chemical sterilants, from the sterilizing chamber, (b) drive a condensing gas, such as steam, into the materials to be or being sterilized to produce condensation on the interstices of the load, (c) revaporize the condensate to humidify the materials and to transport the air or chemical sterilant from the interstices of the load to the sterilizing environment and (d) dilute the air or chemical sterilants from the sterilizing chamber.

It is a further feature of the invention to provide improved sterlization methods and apparatus which use the condensing gas, as a dilutent-carrier substance, at a temperature below that which would degrade the materials being processed.

An advantage of this invention is the decreased risk of exposure to chemical sterilants upon completion of sterilization.

Other objects, features and advantages of the invention will become more apparent from a reading of the following description detailing methods and the presently preferred apparatus in accordance therewith which are shown in the accompanying drawings, in which:

FIG. 2 is a graphic representation of the processes for pre-sterilization air removal and chemical sterilant introduction with time on the y-axis and chamber pressure on the x-axis;

Figure 1:
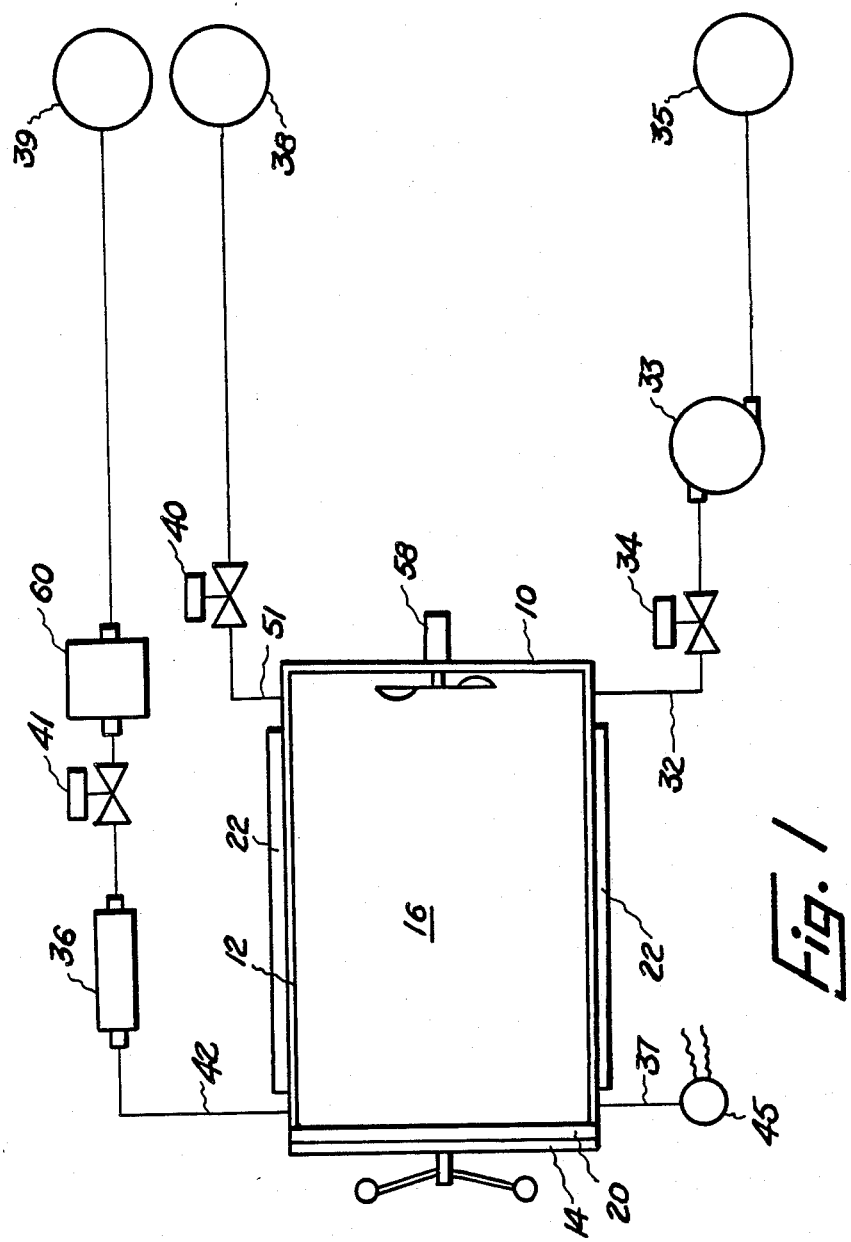
FIG. 1 is a schematic representation of the apparatus embodying the invention.

FIG. 3 is a graphic representation of the processes for chemical sterilant removal with time on the y-axis and chamber pressure on the x-axis; and FIG. 4 is a graphic representation of both the relationship between time and removal of excess non-condensible gases, such as air or chemical sterilant, from the load during a decrease in chamber pressure and the relationship between time and revaporization of the condensing gas in the load, where real time is measured on the x-axis and pack discharge is measured on the y-axis.

Referring to FIG. 1, the sterlizer comprises a chamber structure indicated generally at 10 which consists of an open ended vessel 12, an end closure door 14 and a sterilizing chamber 16. Vessel 12 is combined with a flange 20. The door 14 can be hinged or otherwise mounted to the flange 20 to facilitate opening and closing of the chamber 16. A conventional lock assembly can be used with the door 14 enabling the door to be firmly locked to seal the chamber 16 during the sterlization and detoxification process. The chamber temperature is controlled by a heating strip 22, such as an electric heating strip or any other controlled heating means, which can be set to control the vessel 12 at a predetermined temperature, the wall of the vessel 12. Conduits and controls to perform the sterilization process and the load to be sterilized (e.g., sheets, towels or tubing) are not shown.

A drain line 32 is connected to a vacuum pump 33 through a control valve 34. The output of the vacuum pump is discharged to a vent 35. Valve 34 controls the discharge of fluids through the vacuum pump 33.

Conduit 42 allows a non-condensing gas, such as air or a chemical sterilant, to vent into the sterilizing chamber through a bioretentive filter 60, a control valve 41 and a heat exchanger 36. The gas may be transported from a pressurized source 39 or simply atmospheric air, where appropriate. The heat exchanger 36 is controlled such that the temperature of gas entering the vessel 16 is at a predetermined temperature which will not exceed the temperature limits of the materials being processed.

Conduit 51 allows a condensing gas, such as steam, into the vessel 16 from a steam supply 38 through a control valve 40. A circulation blower 58 is attached to the vessel 12 to provide circulation and uniform environmental conditions in the chamber 16. A pressure transducer 45 is connected to the vessel 12 through conduit 37.

Operation of the sterilization apparatus to remove air from the load and the sterilizing chamber will be apparent from a review of FIG. 2 which diagrams the pressure in the chamber during the sterilization process.

At the beginning of a sterilizing process, the sterlizing chamber environment is room air at substantially atmospheric pressure as shown generally at 101. To initiate the process, the sterilizing chamber is evacuated to an initial vacuum level P1 which is shown at 102. Referring to FIG. 1, this is accomplished by turning on the vacuum pump 33 and opening the vacuum control valve 34 with all other valves closed. This removes the gross quantities of air in the sterilizing chamber 16.

When the pressure P1 is attained, a condensing gas, such as steam, is flushed through the sterilizing chamber 16 while maintaining substantially a constant subatmospheric pressure P1. This is accomplished by modulating the steam control valve 40 on and off relative to the selected pressure P1. The vacuum level P1 is selected such that steam entering the sterilizing chamber will not exceed temperatures the materials can withstand without damage (e.g., searing or melting).

On completion of the timed interval for the flush period shown generally at 103 in FIG. 2, the sterilizing chamber environment is substantially steam and some of the steam penetrates the periphery of the materials. Next, the sterilizing chamber 16 is pressurized with heated air, which has passed through a bioretentive filter 60, or with additional steam to a given presure level P2 as shown generally at 104 of FIG. 2. Air addition is achieved by closing the steam and vacuum control valves 40 and 34 and opening the air in control valve 41 in FIG. 1. If steam is used, steam control valve 40 is modulated until pressure level P2 is reached. Care is taken to insure that the temperature at which damage to the material occurs is not exceeded. In either case, steam is driven into the load. The high pressure compresses steam into the interstices of the load and some of the steam condenses on these surfaces. The chamber is subsequently evacuated to the predetermined pressure P1 as shown at 106 of FIG. 2.

During the evacuation period between 104 and 106, excess air and steam in the chamber 16 are removed. In addition, the condensate begins to revaporize and air and steam are pulled out of the materials into the sterilizing chamber. Evacuation of the chamber 16 is accomplished by opening the vacuum control valve 34 and closing control valves 41 and 40.

Referring to FIG. 4, it was found that there is a time constant between when the excess gases (air and steam) begin to be pulled out of the materials and when the condensate on the materials picks up enough heat energy to be revaporized and begins to be pulled out of the material. This time lag between removal of excess gases and when the material picks up sufficient heat energy, as chamber pressure decreases, to revaporize creates a concentration gradient through the load which allows the vaporized condensate to act as a transport mechanism to carry the air out of the interstices of the materials.

Referring generally to 107 of FIG. 2, the air is flushed from the sterilizing chamber 16 of FIG. 1 in the same way as described for the steam flush configuration shown at 102 to 103 of FIG. 2. The procedure producing the process configuration from 103 to 107 is repeated until air is removed from the system as shown generally at 109.

Following the air removal-humidification process of the present invention, the sterilizing chamber is then pressurized with a sterilant gas, such as ethylene oxide, steam or formaldehyde, to initiate the microbial destruction as shown at 111 of FIG. 2. Because all of the air is removed from the materials and the sterilizing chamber, the sterilant pressure compresses the steam present at 109 in the load and the steam condenses on the surface of the materials. This allows the sterilant to penetrate with the steam into remote areas and interstices of the load which would not ordinarily be accessible.

Table 1 shows a comparison of the effectiveness of conventional humidification processes versus the present process in delivering humidity and sterilant to the inside of tubing (load). The results demonstrate that humidity (Rh) does not penetrate the tubing in a conventional process, but that it does with present invention. Table 1 also shows that chemical sterilant does not penetrate the tubing in the conventional process where it does in the present process, which penetration occurs within 30 minutes.

TABLE 1

| Humidification Time in Minutes | Conventional Ethylene Oxide Sterilization Process Penetration | | Present Invention Penetration | |
| --- | --- | --- | --- | --- |
| | Humidity | Sterilant | Humidity | Sterilant |
| 30 | none | none | 40% Rh | yes |
| 60 | none | none | | |
| 90 | none | none | | |
| 120 | none | none | | |

Referring to FIG. 3, at the end of a sterilizing process, the chamber 16 is pressurized with the sterilant as shown generally at 111. If steam is the sterilant, the pressure is released by opening valve 34 to atmospheric, and the load is allowed to cool before removal from the chamber. To initiate the detoxification process when a chemical sterilant is used, the sterilizing chamber is evacuated to an initial vacuum level P1 which is shown at 112.

Referring to FIG. 1, this is accomplished by turning on the vacuum pump 33 and opening the vacuum control valve 34 with all of the other valves closed. This removes the gross quantities of sterilant in the sterilizing chamber 16.

When the pressure P1 is attained, a condensing gas, such as steam, is flushed through the sterilizing chamber 16 while maintaining substantially a constant pressure P1. This is accomplished by modulating the steam control valve 40 on and off relative to the selected pressure P1.

Referring to FIG. 3, this flushing period is maintained between 112 and 113 to allow more of the sterilant to be diluted in the sterilizing chamber 16. The vacuum level P1 is selected such that steam entering the sterilizing chamber is superheated above the dew point on the surface and on the interstaces of the materials which have been sterilized and the temperature will not exceed temperatures the materials can withstand without damage (e.g., searing or melting).

On completion of the timed interval for the flush period shown generally at 112 to 113 in FIG. 3, the sterilizing chamber environment is substantially steam and some of the steam penetrates the periphery of the materials.

Next, the sterilizing chamber 16 is pressurized with heated air, which has passed through a bioretentive filte 60, or with additional steam to a given level P3 as shown generally at 114 of FIG. 3. Air addition is achieved by closing the steam and vacuum control valves 34 and 40 and opening the air in control valve 41 shown in FIG. 1. If steam is used, control valve 40 is modulated until pressure R3 is reached. Care is taken to insure that the temperature at which damage to the material occurs is not exceeded. In either case, steam is driven into the load. The high pressure compresses the steam in the load and some of the steam condenses on these surfaces. This condensate extracts water soluble sterilants, such as ethylene oxide or formaldehyde, from the materials by producing a low concentration gradient at the surface and the water has a greater attractive force than the material for the sterilant.

For plastic materials, the conpensate is allowed to remain on the surface of the materials for an interval (dwell period) as shown generally at 115 in FIG. 3. After this predetermined dwell period, the chamber is evacuated to the predetermined pressure P1. The extraction dwell period 115 is selected based upon the rate at which the sterilant is extracted from the materials being processed. Paper or cotton materials may require almost no dwell period while plastics may require a 10 minute dwell.

During the evacuation period between 115 and 116, excess air, sterilant and steam are pulled out of the materials into the sterilizing chamber. Evacuation is accomplished by opening the vacuum control valve 34 and closing control valves 41 and 40.

Referring to FIG. 4, it also was found that there is a time constant between when the sterilant gases are pulled out of the materials and when the condensate on the materials picks up enough heat energy to be revaporized and begin to be pulled out of the material. This time lag between removal of excess gases and when the material picks up sufficient heat energy, as chamber pressure decreases, to revaporize creates a concentration gradient through the load which allows the vaporized condensate to carry most of the air (or steam) and sterilant out of the interstices of the materials.

Referring again to 117 of FIG. 3, the air (or steam) and sterilant are flushed from the sterilizing chamber during the period 117 in the same way as described for the steam flush configuration shown at 107 in FIG. 2. The process from 113 to 117 is then repeated until an acceptable sterilant residue level is attained as shown at 119. Two cycles are used in this example, but the duration and number of repetitions may differ because they are related to the type of material being sterilized and its destined usage (e.g., implants, such as pacemakers, may require a higher number of repetitions and longer cycles than other materials, such as towels). The sterilizing chamber is then vented to atmospheric pressure as shown at 121 and the load may be removed. This is accomplished by closing control valves 31 and 40 and opening control valve 41.

Table 2 shows that removal of chemical sterilants by the process ("steam detoxification") of this invention results in much lower residues of sterilant in load then can be safely used. Ambient aeration is described above. Mechanical aeration is carried out by flushing heated, filtered air through the environment and around the materials which have been sterilized. Concentration of residue chemical sterilant was measured by total extraction, gas chromatographic evaluation.

Variations and modifications of the described methods and apparatus, within the scope of the invention, may suggest themselves to those skilled in the art. Accordingly, the foregoing description should be taken as illustrative and not in a limiting sense.

TABLE 2

Ethylene Oxide residue after two hours sterilization at 130° F., 650 mg/l EO & 50% Rh for various packaging materials.

| MATERIAL | CONCENTRATION FOLLOWING STERILIZATION | AMBIENT AERATION 70–75° F. | MECHANICAL AERATION 130° F. | STEAM DETOXIFICATION 130–132° F. |
|---|---|---|---|---|
| Brown Kraft Paper | 4800 ug/g | 24 Hr. 3800 ug/g | Not Tested | 30 min. (ND) |
| Glassine | 4700 ug/g | 24 Hr. 3100 ug/g | Not Tested | 30 min. (ND) |
| Clay Board | 4200 ug/g | 24 Hr. 1100 ug/g | Not Tested | 30 min. (ND) |
| 48 Muslin Towels (pack) | Not Tested | Not Tested | Not Tested | 30 min. (ND) |
| PVC Tubing 2 mm | 11,000 ug/g | 24 Hr. 1074 ug/g | 1.5 Hr. 3166 ug/g | 1.5 Hr. 986 ug/g 2.5 Hr. |

TABLE 2-continued

Ethylene Oxide residue after two hours sterilization at 130° F., 650 mg/1 EO & 50% Rh for various packaging materials.

| MATERIAL | CONCENTRATION FOLLOWING STERILIZATION | AMBIENT AERATION 70–75° F. | MECHANICAL AERATION 130° F. | STEAM DETOXIFICATION 130–132° F. |
|---|---|---|---|---|
| Wall | | | | 624 ug/g |

ND (EO not detected)

I claim:

1. In a method of sterilizing materials with a non-condensable chemical sterilant gas, which sterilizing comprises loading the materials into a sealable chamber and exposing the materials to the non-condensable chemical sterilant gas for a time sufficient to effect sterilization, the improvement comprising removing a non-condensable gas from the interstices of the materials, which removing comprises:

evacuating the chamber to a first subatmospheric pressure, flushing the chamber with steam at said first subatmospheric pressure for a period of time sufficient to substantially flood the chamber with steam, pressurizing the chamber with air or steam to a second subatmospheric pressure, higher than said first subatmospheric pressure, to condense steam within the interstices of the materials, again evacuating the chamber to said first subatmospheric pressure to revaporize steam condensed within the interstices of the materials, which steam transports said non-condensable gas out of the interstices of the materials, and again flushing the chamber with steam at said first subatmospheric pressure for a time sufficient to remove said non-condensable gas from the chamber.

2. The method as set forth in claim 1 wherein the chamber is evacuated to a point sufficient to maintain the temperature in the chamber below that at which the materials loaded into it would be heat damaged.

3. The method as set forth in claim 1 wherein the condensing gas is steam.

4. The method according to claim 1 wherein after said last flushing step a chemical sterilant gas is introduced into the chamber and the chamber pressure is raised to a superatmospheric pressure.

5. The method as set forth in claim 1 wherein the non-condensable gas is a chemical sterilant.

6. The method as set forth in claim 1 wherein the chemical sterilant gas is selected from the group consisting of ethylene oxide and formaldehyde.

7. In a method of sterilizing materials which comprises loading the materials into a sealable chamber and exposing the materials to a sterilant for a time sufficient to effect sterilization, the improvement comprising removing a non-condensable gas from the interstices of the materials prior to treatment with the sterilant, which removing comprises:
   (a) depressurizing said chamber to a first subatmospheric pressure,
   (b) introducing a condensable gas at said first subatmospheric pressure into said chamber to flush said chamber,
   (c) pressurizing said chamber to a second subatmospheric chamber, higher that said first subatmospheric chamber, with heated air or a condensable gas to condense the condensable gas in the interstices of materials loaded in said chamber,
   (d) evacuating said chamber to said first subatmospheric pressure for a time sufficient to revaporize condensed gas in the interstices of the materials and to purge the non-condensable gas and the condensable gas from the interstices of the materials in said chamber, and
   (e) repeating steps (b) through (d) for a plurality of times to effectively remove said non-condensable gas from the interstices of the materials in the chamber.

8. The method as set forth in claim 7 wherein the chamber is depressurized to a point sufficient to maintain the temperature in the chamber below that at which the materials loaded into the chamber would be heat damaged.

9. The method as set forth in claim 7 wherein the steps are repeated until all the non-condensable gas is removed.

10. The method as set forth in claim 7 wherein the condensable gas is steam.

11. The method as set forth in claim 7 wherein the non-condensable gas is air.

12. In a method of sterilizing material with a non-condensable chemical sterilant gas, which sterilizing comprises loading the materials into a sealable chamber and exposing the materials to the non-condensable chemical sterilant gas for a time sufficient to effect sterilization, the improvement comprising removing said non-condensable chemical sterilant gas from the interstices of materials loaded in said chamber subsequent to sterilizing, which removal comprises:
   (a) depressurizing said chamber to a first subatmospheric pressure,
   (b) introducing a condensable gas at said first subatmospheric pressure into said chamber to flush said chamber,
   (c) pressurizing said chamber to a second subatmospheric chamber, higher than said first subatmospheric chamber, with heated air or a condensable gas to condense said condensable gas in the interstices of the materials loaded in said chamber,
   (d) evacuating said chamber to said first subatmospheric pressure for a time sufficient to revaporize condensed gas in the interstices of the materials and to purge the non-condensable chemical sterilant gas and the condensable gas from the interstices of the materials in said chamber, and
   (e) repeating steps (b) through (d) for a plurality of times to effectively remove said non-condensable chemical sterilant gas from the interstices of the materials in said chamber.

13. The method as set forth in claim 12 wherein the chamber is depressurized to a point sufficient to maintain the temperature in the chamber below that at which the materials loaded into the chamber would be heat damaged.

14. The method as set forth in claim 12 wherein the steps are repeated until the non-condensable chemical sterilant gas is removed.

15. The method as set forth in claim 12 wherein the chemical sterilant is selected from the group consisting of ethylene oxide and formaldehyde.

* * * * *